United States Patent [19]
Felt

[11] Patent Number: 5,352,371
[45] Date of Patent: Oct. 4, 1994

[54] METHOD AND APPARATUS FOR REPEATEDLY PASSING A FLUID THROUGH A FLUID TREATMENT UNIT

[75] Inventor: Thomas J. Felt, Boulder, Colo.

[73] Assignee: Cobe Laboratories, Inc., Lakewood, Colo.

[21] Appl. No.: 21,885

[22] Filed: Feb. 24, 1993

[51] Int. Cl.$^5$ .............................................. B01D 21/26
[52] U.S. Cl. .................................. 210/787; 210/252; 210/418; 210/782
[58] Field of Search .................. 210/85, 94, 97, 195.2, 210/199, 252, 239, 240, 252, 360.1, 418, 433.1, 434, 512.1, 645, 767, 782, 789; 604/6, 80, 82, 258, 262; 137/596, 597; 138/40, 104, 111, 118

[56] References Cited
U.S. PATENT DOCUMENTS

| | | |
|---|---|---|
| 2,357,238 | 8/1944 | Trimble . |
| 2,485,842 | 10/1949 | Pennington . |
| 3,291,151 | 12/1966 | Loken . |
| 3,730,170 | 5/1973 | Michael . |
| 4,051,852 | 10/1977 | Villari ............................. 137/512.3 |
| 4,219,021 | 8/1980 | Fink ................................ 137/556.6 |
| 4,257,416 | 3/1981 | Prager .................................. 604/52 |
| 4,306,976 | 12/1981 | Bazzato ............................... 210/646 |
| 4,335,717 | 6/1982 | Bujan et al. ........................... 604/83 |
| 4,364,383 | 12/1982 | Vcelka ................................ 604/407 |
| 4,425,116 | 1/1984 | Bilstad et al. .......................... 604/6 |
| 4,526,515 | 7/1985 | DeVries ................................ 604/6 |
| 4,691,738 | 9/1987 | McCune ............................. 137/597 |
| 4,796,644 | 1/1989 | Polaschegg ............................ 604/4 |
| 4,850,995 | 7/1989 | Tie et al. ................................ 604/6 |
| 5,049,128 | 9/1991 | Duquette ............................... 604/83 |

FOREIGN PATENT DOCUMENTS 2143803 2/1985 United Kingdom .

OTHER PUBLICATIONS

Brochure from Travenol Laboratories, Inc. entitles "An Advanced Line of Blood Sets Designed to Simplify & Improve Dialysis Therapy" (1984).
COBE Labratories, Inc. Spectra White Blood Cell Set Instructions for Use (1990).
Brochure on COBE Spectra System from COBE Labratories, Inc. (1991).
Information Packet from COBE Laboratories, Inc. entitled "A Complete System for Your Monitoring Needs" (1982).

*Primary Examiner*—Robert A. Dawson
*Assistant Examiner*—Sun Uk Kim
*Attorney, Agent, or Firm*—Jay K. Malkin

[57] ABSTRACT

A method and apparatus for the multiple passage of fluids through a treatment unit (e.g. a medical apheresis unit). The apparatus includes primary and secondary vessels. Connected to the primary vessel is a first conduit which terminates at the treatment unit outlet, and a second conduit which terminates at the treatment unit inlet. Connected to the secondary vessel is a third conduit which terminates at the treatment unit inlet, and a fourth conduit which terminates at the treatment unit outlet. In use, a clamp is simultaneously secured to the first conduit and second conduit prior to filling the primary vessel with fluid (e.g. bone marrow). The clamp is then removed and placed on the first conduit and the third conduit simultaneously so that fluid flows from the primary vessel, into the treatment unit, and into the secondary vessel. The clamp is then removed and positioned on the second conduit and the fourth conduit simultaneously so that fluid flows from the secondary vessel, through the treatment unit, and back into said primary vessel, thereby completing two passes of fluid through the treatment unit using a single clamp. Additional passes may be accomplished by repeating the foregoing steps. Also, conduit attachment members or clamp position indicating members may be applied to the conduits to facilitate proper use of the entire system.

24 Claims, 4 Drawing Sheets

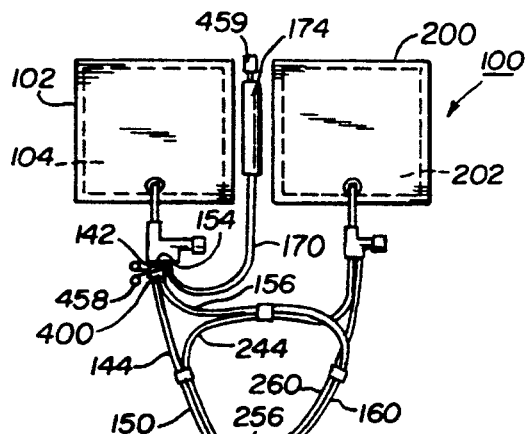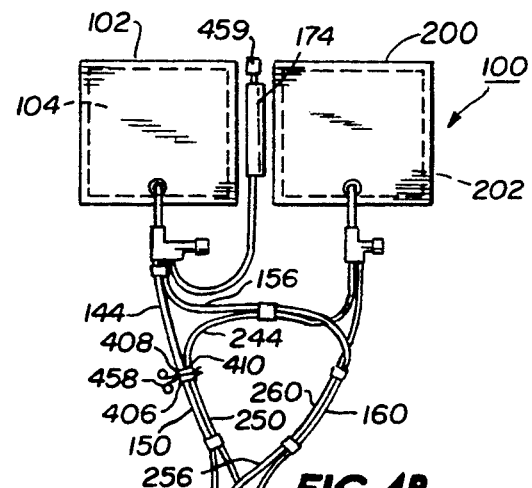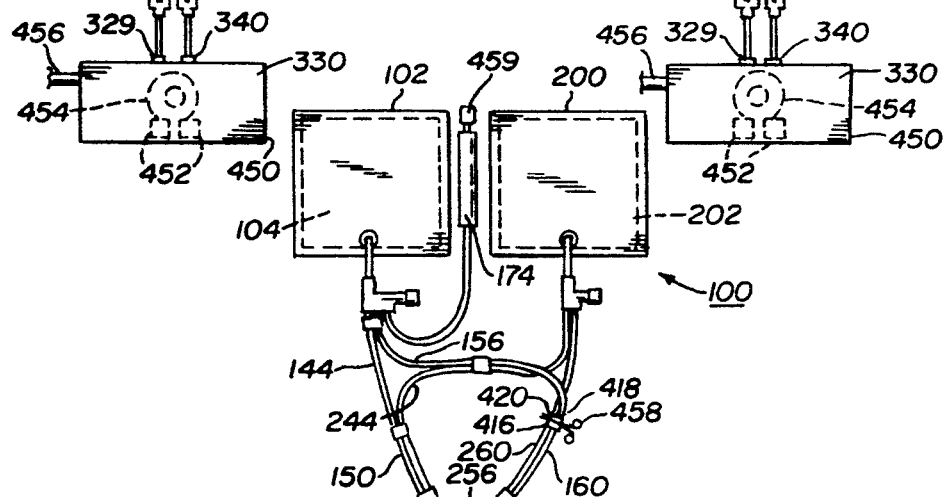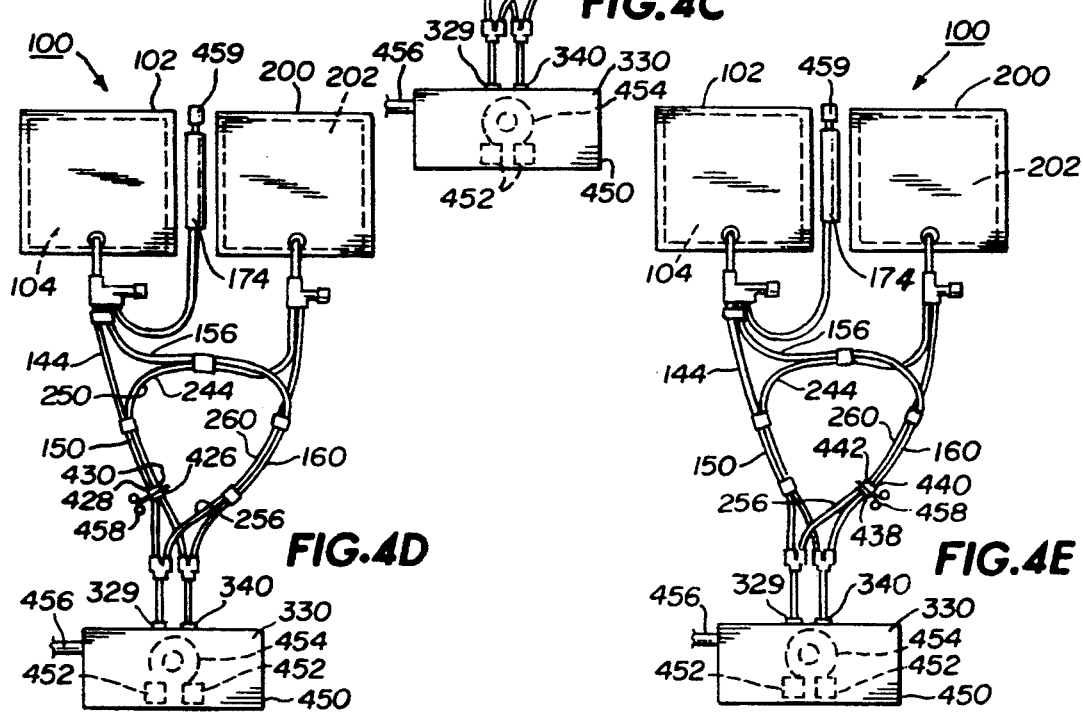

METHOD AND APPARATUS FOR REPEATEDLY PASSING A FLUID THROUGH A FLUID TREATMENT UNIT

The present invention generally relates to the physical and chemical treatment of fluid materials, and more particularly to a system for repeatedly passing a fluid through a fluid treatment unit in order to enhance the treatment process.

Recent developments in medical and chemical technology have created a corresponding need for high-efficiency fluid treatment systems. In particular, high-efficiency fluid treatment systems are especially important in a wide variety of technical fields ranging from the treatment of bodily fluids (e.g. blood, bone marrow, and the like) for the removal/separation of specific components therefrom to the treatment of water or other fluids to remove solid contaminants. Of particular interest is the separation of components from bodily fluids in a process known as "apheresis". The term "apheresis" involves a procedure wherein various components may be removed from fluid materials using a variety of techniques including but not limited to centrifugal separation. Apheresis systems are useful for a wide variety of medical applications including but not limited to: (1) the removal of blood plasma for donation or therapeutic purposes from a human subject without the loss of cellular blood components; and (2) the removal of lymphocytes from patients afflicted with chronic lymphocytic leukemia (as described in Dutcher, J.P. et al, "Lymphocytopheresis for Killer Cell Generation in Patients with Chronic Lymphocytic Leukemia: Comparison of COBE 2997 and COBE Spectra", *Clinical Journal of Apheresis*, Vol. 5, Issue 1:38 (1989) which is incorporated herein by reference. Another important apheresis procedure involves the removal of mononuclear cells from the bone marrow of patients afflicted with various forms of cancer ranging from brain cancer to renal cell melanoma. The term "mononuclear cells" as used herein basically involves cell structures associated with a patient's immune system including but not limited to lymphocytes, monocytes, and stem cells. Lymphocytes consist of white blood cells (e.g. "leukocytes") which recognize specific antigen materials. Because of this ability, lymphocytes only attack invading cellular materials, and avoid normal, healthy cells. Monocytes involve another type of white blood cell (within a subclass known as "phagocytes") which are able to "phagocytize" or engulf foreign materials. Finally, stem cells consist of precursor cell structures from which all other blood cells originate (including those listed above) in a process known as "hemopoiesis". A minimal amount of specific information exists regarding stems cells and the functional capabilities thereof. For example, the exact mechanism used by stem cells to differentiate into various blood structures is currently unknown. However, it is substantially certain that stem cells originate and reside within bone marrow, along with the other immunological components described above.

The treatment of various cancers may involve radiation therapy or the administration of chemotherapeutic agents. These materials and procedures are designed to destroy malignant tissues in a patient, but may also destroy other cellular structures, including the mononuclear cells listed above (e.g. stem cells, monocytes, or lymphocytes) which comprise the patient's immune system. This problem may be avoided by removing the foregoing components from the patient's bone marrow (which is fluidic in character) using a medical apheresis system, and administering the selected treatment therapy. When treatment of the patient is completed, the previously-removed components of the patient's immune system are then readministered. Using this technique, the patient's immune system is protected from the harmful effects of radiation or chemotherapy, thereby increasing the probability of a successful recovery. The recovery of mononuclear cell materials using apheresis is basically described in Hester, J.P., et al., "Peripheral Blood Mononuclear-Stem Cell (PBMSC) Collection in Two Continuous Flow Cell Separators: Yields (Y) and Crosscellular Contamination", *Clinical Journal of Apheresis*, Vol. 5, Issue 1:41 (1989) which is also incorporated herein by reference.

When fluids (e.g. blood, bone marrow, water, and other materials) are treated using the foregoing processes, it is often necessary to pass the fluids through the selected treatment unit numerous times to ensure complete treatment. This is especially important in apheresis procedures which may require the multiple treatment of a selected fluid in order to recover a maximum amount of desired components. For example, the efficiency of an apheresis apparatus in recovering a particular desired type of cell (e.g. stem cells) from a bodily fluid (e.g. bone marrow) may be approximately expressed as a percentage of the total number of that type of cell present in the fluid. This efficiency of recovery may be approximately the same each time the fluid is passed through the apheresis apparatus. Thus, if the apheresis apparatus will recover sixty percent of the desired cells during a first pass through the apparatus, a second pass will recover sixty percent of the remaining desired cells, bringing the total recovery to approximately eighty four percent of the cells originally present in the fluid. A third pass would recover sixty percent of the remaining desired cells, bringing the total recovery to approximately ninety three percent. A fourth pass would bring the total recovery of desired cells in this example to approximately ninety seven percent of the desired cells originally present in the fluid.

The present invention involves a method and apparatus for repeatedly passing a fluid through a fluid treatment unit which enables fluid treatment to occur in a rapid, complete, and highly-efficient manner. The invention is readily applicable to a wide variety of fluid treatment units (including numerous commercially available systems), and therefore represents an advance in the art of fluid treatment/separation.

SUMMARY OF THE INVENTION

It is an object of the present invention to provide a highly-efficient system for treating fluid materials.

It is another object of the invention to provide a highly-efficient system for treating fluid materials which may be used for a variety of different purposes.

It is a another object of the invention to provide a method and apparatus for facilitating the multiple passage of fluid materials through a selected fluid treatment unit in order to achieve maximum fluid treatment efficiency.

It is a further object of the invention to provide a method and apparatus for facilitating the multiple passage of fluid materials through a selected fluid treatment unit in which maximum treatment efficiency is achieved using a minimal number of components.

It is a still further object of the invention to provide a method and apparatus for facilitating the multiple passage of fluid materials through a selected fluid treatment unit in which maximum treatment efficiency is achieved using a minimal number of process steps.

It is an even further object of the invention to provide a method and apparatus for facilitating the multiple passage of fluid materials through a selected fluid treatment unit which accomplishes all of the foregoing objectives and is particularly applicable to the medical apheresis of bodily fluids (e.g. the removal/concentration of desired components from blood or bone marrow).

In accordance with the foregoing objects, the present invention involves a method and apparatus for accomplishing the treatment of fluid materials in a highly efficient manner. The term "treatment" as used herein shall broadly involve the chemical or physical processing of fluid materials to remove or separate selected components therefrom. A wide variety of treatment processes are prospectively applicable in connection with the present invention, including but not limited to the separation of various components from each other in bodily fluids (e.g. the removal of desired components from blood, bone marrow, and the like), the removal of suspended solids from water, and the separation of desired materials (e.g. metallic solids and the like) from liquid industrial wastes. Thus, while particular reference may be made herein to specific treatment processes which can be used in accordance with the invention, it shall not be limited to any specific treatment unit or system.

To achieve maximum efficiency using a selected fluid treatment unit, it is often necessary to repeatedly pass the desired fluid through the unit. This is especially important in the apheresis of bodily fluids (e.g. blood or bone marrow) wherein one or more components are being removed therefrom. To accomplish this goal in accordance with the present invention, a unique fluid transfer assembly adapted for attachment to the selected fluid treatment unit is disclosed herein. The fluid transfer assembly enables the multiple passage of fluid materials through the fluid treatment unit in a highly efficient manner using a minimal number of components and process steps.

The fluid transfer assembly of the present invention basically involves a primary vessel and a secondary vessel, each having an interior region therein designed for retaining the fluid being treated. Operatively connected to the primary vessel and in fluid communication with the interior region thereof is the proximal end of a tubular first conduit. The first conduit further includes a distal end and a medial portion between the proximal end and the distal end. The distal end of the first conduit is operatively connected to and in fluid communication with the outlet of a selected fluid treatment unit. Likewise, operatively connected to the primary vessel and in fluid communication with the interior region thereof is the proximal end of a tubular second conduit. The second conduit further includes a distal end and a medial portion between the proximal end and the distal end. The distal end of the second conduit is operatively connected to and in fluid communication with the inlet of the fluid treatment unit.

The fluid transfer assembly described herein further includes a tubular third conduit having a proximal end, a distal end, and a medial portion between the proximal end and the distal end. The proximal end of the third conduit is operatively connected to the secondary vessel and in fluid communication with the interior region thereof. The distal end of the third conduit is operatively connected to and in fluid communication with the inlet of the fluid treatment unit. Finally, the fluid transfer assembly includes a fourth conduit. having a proximal end, a distal end, and a medial portion between the proximal end and the distal end. The proximal end of the fourth conduit is operatively connected to the secondary vessel and in fluid communication with the interior region thereof. Likewise, the distal end of the fourth conduit is operatively connected to and in fluid communication with the outlet of the fluid treatment unit.

The foregoing components (especially the conduits) are preferably configured to form a completed fluid transfer assembly which is compact and easy to use. To accomplish these goals, the first, second, third, and fourth conduits are preferably secured together in a unique configuration which enables multiple conduits (e.g. conduit pairs) to be simultaneously clamped using a single clamp. In a preferred embodiment, first attachment means is provided for securing the medial portion of the second conduit to the medial portion of the third conduit. Second attachment means is likewise provided for securing the medial portion of the first conduit to the medial portion of the third conduit, with the second attachment means being remotely spaced from the first attachment means. Finally, third attachment means is provided for securing the medial portion of the fourth conduit to the medial portion of the second conduit, with the third attachment means being remotely spaced from the first attachment means. In this configuration, all of the conduits form a compact structure wherein the simultaneous clamping of conduit pairs is facilitated.

To secure the foregoing conduits together as described above, the first attachment means, second attachment means, and third attachment means may involve a plurality of different structures including but not limited to portions of adhesive tape, plastic bands, clips, wire members, string, and the like. Furthermore, in order to produce the desired compact arrangement of conduits set forth herein, it is preferred that (1) the second conduit is longer than the first conduit; (2) the third conduit is longer than the fourth conduit; (3) the first and fourth conduits are approximately equal in length; and (4) the second and third conduits are approximately equal in length.

It is also preferred that the first and fourth conduits (which terminate at the outlet of the fluid treatment unit) are marked with indicia (e.g. a continuous stripe) of a first color. The second and third conduits (which terminate at the inlet of the fluid treatment unit) are likewise marked with indicia a continuous stripe) of a second color which is different from the first color. The use of different colored indicia enables the foregoing conduits to be rapidly identified/distinguished by the system operator.

In a further preferred embodiment, the fluid transfer assembly includes a plurality of clamp position indicating members which identify the proper order in which selected conduit pairs are clamped during fluid treatment. The clamp position indicating members may involve a variety of different structures, including but not limited to tags, labels, bands, and comparable structures applied to the conduits of interest. Furthermore, individual portions of adhesive tape wrapped around the selected conduits may also be used for clamp position identification. If adhesive tape or other materials are used, they may be applied to the selected conduit pairs either in addition to or instead of the multiple attachment means set forth above. In addition, specific indicia may be applied to the clamp position indicating members to thereby designate the order in which various conduit pairs are to be clamped. Exemplary indicia suitable for this purpose include but are not limited to sequential numeric or alphabet characters.

If clamp position indicating members are used, at least three members will be placed at various positions on the conduits of the fluid transfer assembly so that selected conduit pairs may be clamped simultaneously. Specifically, the first clamp position indicating member is placed on the first conduit and the second conduit at the proximal ends thereof so that the proximal ends are adjacent to and against each other. The second clamp position indicating member is placed on the media portions of the first conduit and the third conduit so that the medial portions thereof are adjacent to and against each other. The third clamp position indicting member is placed on the medial portions of the second conduit and the fourth conduit so that the medial portions thereof are adjacent to and against each other. Optional fourth and fifth clamp position indicating members may also be attached to the conduits of the fluid transfer assembly. Specifically, the fourth clamp position indicating member is secured to the medial portions of the first conduit and the third conduit so that the medial portions thereof are adjacent to and against each other at a position remotely spaced from the second clamp position indicating member. Likewise, the fifth clamp position indicating member is secured to the medial portions of the second conduit and the fourth conduit so that the medial portions thereof are adjacent to and against each other at a position remotely spaced from the third clamp position indicating member.

In order to achieve the multiple passage of a fluid through a selected fluid treatment unit (e.g. an apheresis unit designed to remove various components from blood, bone marrow, and the like), a conventional clamp is first secured to said first conduit and said second conduit simultaneously (at the first clamp position indicating member, if used). Thereafter, the primary vessel is supplied with a fluid to be treated. The fluid may optionally be passed through at least one filter prior to entry into the primary vessel. Next, the clamp is removed from the first conduit and the second conduit when treatment of the fluid is desired. The clamp is then secured to the first conduit and the third conduit simultaneously (at the second clamp position indicating member, if used) in order to allow fluid to flow out of the primary vessel, into the second conduit, and into the inlet of the treatment unit. The fluid then passes through the treatment unit (which preferably includes at least one pump therein) and out of the treatment unit through the outlet. The fluid thereafter passes from the outlet through the fourth conduit and into the secondary vessel. In order to pass the fluid within the secondary vessel back into the treatment unit for further processing/component removal, the clamp is removed from the first conduit and the third conduit. Thereafter, the clamp is positioned on the second conduit and the fourth conduit simultaneously (at the third clamp position indicating member, if used) in order to permit fluid within the secondary vessel to flow into the third conduit and through the inlet of the treatment unit. After passing through the treatment unit, the fluid flows through the outlet, into the first conduit, and back into the primary vessel. Using the foregoing procedure, the selected fluid will be passed through the treatment unit twice using a minimal number of components and process steps compared with previously-known methods. Specifically, in accordance with the foregoing procedure, multiple fluid passage will be accomplished using only four main conduits, a single clamp, and only three clamp movements. Furthermore, with each passage of the fluid through the treatment unit, additional components of interest are collected.

Should additional passages of the fluid through the treatment unit be desired (e.g. in accordance with medical apheresis processes), the clamp is removed from the second conduit and the fourth conduit. The first conduit and the third conduit are then clamped simultaneously using the clamp member (at the fourth clamp position indicating member, if used) in order to allow fluid to flow out of the primary vessel, into the second conduit, and through the inlet of the treatment unit. The fluid then passes through the treatment unit and outwardly therefrom via the outlet. The fluid thereafter passes from the outlet through the fourth conduit and back into the secondary vessel. To pass the fluid within the secondary vessel back into the treatment unit for further treatment, the clamp is removed from the first conduit and the third conduit. The clamp is then positioned on the second conduit and the fourth conduit simultaneously (at the fifth clamp position indicating member, if used) in order to permit fluid within the secondary vessel to flow through the third conduit and back into the inlet of the treatment unit. After passing through the treatment unit and the outlet thereof, the fluid passes into the first conduit and back into the primary vessel. Further passage of the fluid through the treatment unit may be accomplished by repeating the previous two process steps as many times as desired.

The present invention enables the multiple passage of a fluid through a selected fluid treatment unit in a highly efficient manner using a minimal number of process steps and components. It is prospectively applicable to a wide variety of treatment units, and is especially useful in the removal of selected components from bodily fluids including but not limited to blood or bone marrow. Accordingly, the invention represents an advance in the art of fluid treatment. These and other objects, advantages, and features of the invention will be described below in the following Brief Description of the Drawings and Detailed Description of Preferred Embodiments.

BRIEF DESCRIPTION OF THE DRAWINGS

FIGS. 1a–1c collectively illustrate a multi-clamp fluid transfer assembly and the clamp movements associated therewith which enable the multiple passage of a fluid through a selected fluid treatment unit in accordance with previously known methods and materials.

FIGS. 4a–4e collectively illustrate the fluid transfer assembly of FIG. 3 and clamp movements associated therewith which enable the multiple passage of a fluid through a selected fluid treatment unit in accordance with the invention.

DETAILED DESCRIPTION OF PREFERRED EMBODIMENTS

As stated above, the present invention involves a method and apparatus which enable the multiple passage of a fluid through a selected fluid treatment unit in a highly efficient manner. The apparatus and method described herein use a minimal number of components and process steps. Likewise, they are prospectively applicable to a wide variety of fluid treatment units ranging from apheresis systems designed to remove various components from blood, bone marrow, and other bodily fluids to water purification systems and industrial waste treatment units. Thus, notwithstanding the description of specific fluid treatment units herein, the present invention shall not be limited to use in connection with any specific treatment unit. Further information regarding the various treatment units with which the invention may be used will be described below.

As previously indicated, the multiple passage of a fluid through a selected fluid treatment unit is important for a variety of reasons. In medical apheresis procedures where specific components are to be removed from blood, bone marrow, or other bodily fluids, a maximum degree of separation efficiency is important. This may be accomplished by passing the bodily fluid through the selected apheresis unit numerous times. Likewise, when other fluids are being treated to remove harmful or undesirable materials therefrom (e.g. during the treatment of water or other liquids), it is important to achieve a substantially pure final product. To enable a maximum degree of purification, the selected fluid is passed through the treatment unit numerous times to remove as many undesirable products as possible.

Figure 1C:
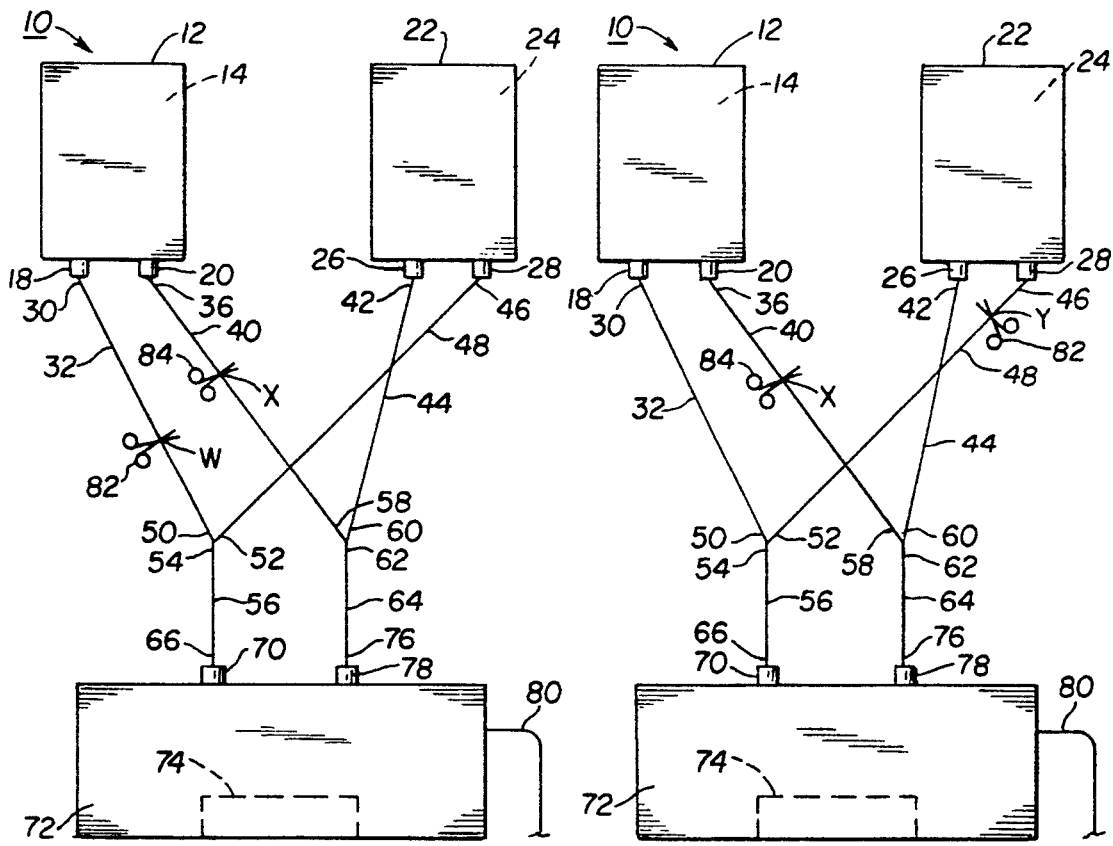
Figure 1C:
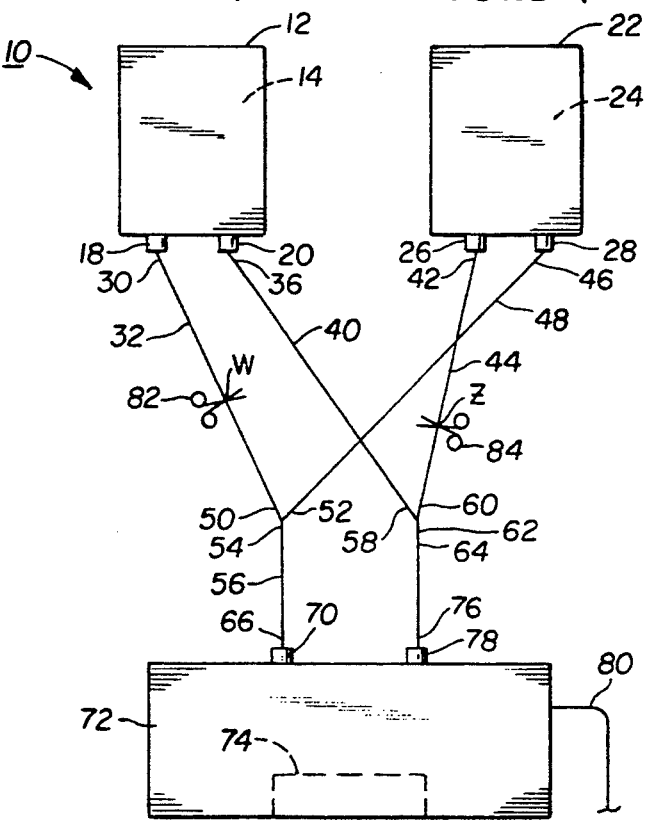

FIGS. 1a–1c schematically illustrate a method and apparatus previously known and used for the multiple passage of fluids through a selected treatment unit. With particular reference to FIG. 1a, a multi-pass system 10 is illustrated which includes a primary vessel 12 in the form of a plastic bag structure having an interior region 14 therein for holding fluid materials. The primary vessel 12 further includes a first port 18 and a second port 20, both of which enable communication with the interior region 14 of the primary vessel 12. Likewise, the system 10 also includes a secondary vessel 22 in the form of a plastic bag structure which is substantially identical to the primary vessel 12. The secondary vessel 22 further includes an interior region 24 therein for holding fluid materials. Access to the interior region 24 is provided through a first port 26 and a second port 28 illustrated in FIG. 1a.

Operatively connected to and in fluid communication with the first port 18 of the primary vessel 12 is the proximal end 30 of a tubular first conduit 32. Likewise, the second port 20 of the primary vessel 12 is operatively connected to and in fluid communication with the proximal end 36 of a tubular second conduit 40 as illustrated.

With continued reference to FIG. 1a, the first port 26 of the secondary vessel 22 is operatively connected to and in fluid communication with the proximal end 42 of a tubular third conduit 44. Finally, the second port 28 of the secondary vessel 22 is operatively connected to and in fluid communication with the proximal end 46 of a tubular fourth conduit 48.

The distal end 50 of the first conduit 32 and the distal end 52 of the fourth conduit 48 are both connected to and in fluid communication with the proximal end 54 of a tubular fifth conduit 56 as illustrated. Likewise, the distal end 58 of the second conduit 40 and the distal end 60 of the third conduit 44 are both connected to and in fluid communication with the proximal end 62 of a tubular sixth conduit 64. In turn, the distal end 66 of the fifth conduit 56 is connected to the inlet port 70 of a fluid treatment unit 72 which is schematically illustrated in FIG. 1a. Once again, the fluid treatment unit 72 may be selected from a variety of different treatment systems known in the art ranging from an apheresis system for selectively removing various components from bodily fluids to a conventional water treatment unit using chemical flocculants. While various systems may be used as the fluid treatment unit 72, the selected unit 72 will preferably include at least one pump 74 associated therewith (e.g. of the conventional peristaltic variety) in order to move fluid through the treatment unit 72.

With continued reference to FIG. 1a, the distal end 76 of the sixth conduit 64 is connected to the outlet port 78 of the fluid treatment unit 72. It should also be noted that the fluid treatment unit 72 further includes a delivery conduit 80 extending outwardly therefrom for the delivery of collected materials (e.g. residual solid matter, blood/bone marrow components, or the like) from the treatment unit 72 to a selected containment vessel (not shown).

In order to achieve the multiple passage of a selected fluid through the treatment unit 72 using the multi-pass system 10 illustrated in FIGS. 1a–1c, the primary vessel 12 is first supplied with a selected fluid to be treated in the treatment unit 72. The fluid may involve a number of different materials, including but not limited to blood, bone marrow, or water. However, prior to supplying the primary vessel 12 with fluid, a clamp 82 of conventional construction is applied to the first conduit 32 at position "W", and a clamp 84 is applied to the second conduit 40 at position "X" as shown in FIG. 1a. In this manner, fluid flow through the first conduit 32 and the second conduit 40 is entirely restricted. It is important to note that the multi-pass system 10 uses a plurality of clamps (e.g. clamps 82, 84) which require multiple, properly-coordinated procedures as described in greater detail below.

When treatment of the fluid in the primary vessel 12 is desired, clamp 82 is moved from position "W" to position "Y" on the fourth conduit 48 as illustrated in FIG. 1b in order to restrict fluid flow therethrough. In this configuration (with clamp 82 at position "Y" and clamp 84 at position "X") fluid from the interior region 14 of the primary vessel 12 is able to flow through the first conduit 32 into the fifth conduit 56, and into the fluid treatment unit 72 via the inlet port 70. Premature fluid flow into the secondary vessel 22 via the fourth conduit 48 is prevented due to the restriction thereof by clamp 82 at position "Y". After being processed within the fluid treatment unit 72, the fluid is then pumped by the pump 74 out of the treatment unit 72 via the outlet port 78. Thereafter, the fluid passes upwardly through the sixth conduit 64 and into the secondary vessel 22 via the third conduit 44. Fluid passage back into the primary vessel 12 via the second conduit 40 is prevented due to the restriction thereof caused by the second clamp 84 at position "X".

In order to pass the fluid within the secondary vessel 22 back into the fluid treatment unit 72 for further processing, clamp 82 is moved from position "Y" back to position "W" on the first conduit 32, with clamp 84 being moved from position "X" on the second conduit 40 to position "Z" on the third conduit 44 as illustrated in FIG. 1c. As a result, fluid within the secondary vessel 22 may pass downwardly through the fourth conduit 48, into the fifth conduit 56, and into the inlet port 70 of the fluid treatment unit 72 for additional processing. Premature fluid flow from the secondary vessel 22 into the primary vessel 12 via the first conduit 32 is prevented due to the restriction thereof by clamp 82 at position "W". Next, the fluid within the fluid treatment unit 72 is pumped by the pump 74 out of the treatment unit 72 via the outlet port 78. The fluid then moves through the sixth conduit 64, into the second conduit 40, and back into the primary vessel 12, thereby completing two passes of the fluid through the fluid treatment unit 72. It should be noted that fluid flow back into the secondary vessel 22 via the third conduit 44 is prevented due to the restriction thereof by clamp 84 at position "Z".

Additional passages of the fluid through the treatment unit 72 by the foregoing multi-pass system 10 may be accomplished by repeating the foregoing clamping steps set forth above as many times as desired.

While the multi-pass system 10 and method associated therewith enable a fluid material to be repeatedly passed through a fluid treatment unit 72 as set forth above, system 10 requires the use of two separate clamps in order to accomplish multi-pass processing. Furthermore, in order to achieve two separate passes of the fluid through the fluid treatment unit 72, clamp 82 must be moved twice (e.g. from its initial location at position "W" to position "Y" and back to position "W"), while clamp 84 must be simultaneously moved from its initial location at position "X" to position "Z". The multiple shifting of a plurality of clamps in the foregoing manner requires numerous manual operations, thereby increasing the possibility of human error with respect to clamp movement, timing, and position.

In direct contrast, the present invention involves a unique method and apparatus which reduces the number of required clamps and clamp movements. As a result the possibility of human error during a fluid treatment procedure is substantially eliminated.

Figure 2:
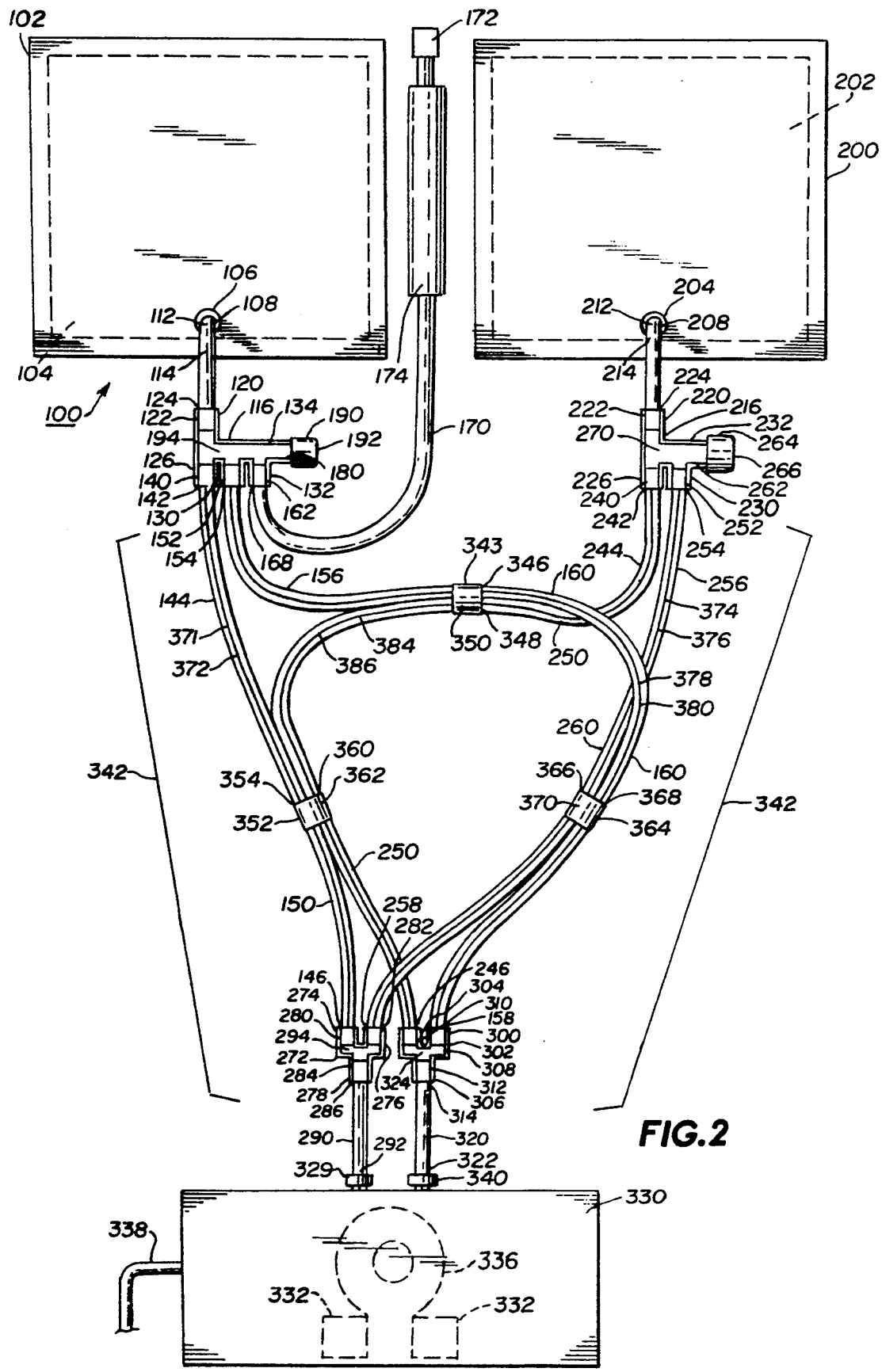
FIG. 2 illustrates a preferred embodiment of a fluid transfer assembly produced in accordance with the present invention which enables the multiple passage of a fluid through a selected fluid treatment unit.

With reference to FIG. 2, a preferred embodiment of a multi-pass fluid transfer assembly 100 is illustrated. As shown in FIG. 2, the assembly 100 includes a primary vessel 102 which, in a preferred embodiment, consists of a transparent, flexible bag structure constructed of an inert plastic material including but not limited to polyvinyl chloride. The primary vessel 102 further includes an interior region 104 therein designed to retain a selected fluid inside the primary vessel 102. Access to the interior region 104 is accomplished through the use of an outwardly extending connecting portion 106 having a bore 108 therein which is in fluid communication with the interior region 104 of the primary vessel 102. Fixedly positioned within the bore 108 is the proximal end 112 of a tubular connecting conduit 114. The term "tubular" as used herein shall generally signify an elongate structure having a bore or passageway therethrough surrounded by a continuous wall. The connecting conduit 114 is preferably manufactured of a resilient, elastomeric material which is substantially inert and suitable for the transfer of biological materials therein (e.g. blood or bone marrow). An exemplary and preferred material which may be used to construct the connecting conduit 114 is polyvinyl chloride. Unless otherwise indicated, all of the conduits described and illustrated herein are preferably manufactured of the same material used to construct the connecting conduit 114 (e.g. polyvinyl chloride or other comparable inert plastic composition).

The proximal end 112 of the connecting conduit 114 is preferably larger in diameter than the diameter of the bore 108 so that the proximal end 112 may be urged into the bore 108 and retained therein by resilient frictional engagement of the proximal end 112 and the interior walls (not shown) of the bore 108. Likewise, to retain the proximal end 112 of the connecting conduit 114 within the bore 108, a suitable solvent (e.g. cyclohexanol) may be applied in a conventional manner to the proximal end 112 or the interior walls of the bore 108. As a result, when these two components are placed in contact with each other, solvation of the plastic materials used to construct them will cause adhesion of the proximal end 112 to and within the bore 108.

With continued reference to FIG. 2, a first multi-port connector 116 is provided which is preferably manufactured of an inert, biologically compatible plastic material (e.g. polyvinyl chloride) that is transparent as shown so that fluid flow therethrough may be observed. The multi-port connector 116 further includes a tubular first port 120 having a bore 122 therein. Fixedly secured within the bore 122 is the distal end 124 of the connecting conduit 114. Unless otherwise indicated, the phrase "fixedly secured" as used herein with respect to the attachment of a conduit within a bore shall preferably involve a system in which (1) the conduit has a greater diameter than its respective bore so that the conduit may be urged into the bore and frictionally engaged therein; and (2) the conduit is also secured within the bore using a suitable solvent in the same manner described above regarding affixation of the proximal end 112 of the connecting conduit 114 within the bore 108.

The multi-port connector 116 further includes a tubular second port 126, a tubular third port 130, a tubular fourth port 132, and a tubular fifth port 134 all of which extend outwardly from the connector 116. With continued reference to FIG. 2, the second port 126 has a bore 140 therein. Fixedly secured within the bore 140 is the proximal end 142 of a tubular first conduit 144. The first conduit 144 further includes a distal end 146 and a medial portion 150 between the proximal end 142 and the distal end 146.

The third port 130 further includes a bore 152 therein. Fixedly secured within the bore 152 is the proximal end 154 of a tubular second conduit 156. The second conduit 156 also includes a distal end 158 and a medial portion 160 between the proximal end 154 and the distal end 158. In a preferred embodiment, the second conduit 156 is longer than the first conduit 144, with the second conduit 156 optimally being about 1.5–2.0 times as long as the first conduit 144.

As illustrated in FIG. 2, the fourth port 132 likewise has a bore 162 therein. Fixedly secured within the bore 162 is the proximal end 168 of a tubular supply conduit 170 which is operatively connected to a schematically-illustrated supply 172 of fluid to be treated (e.g. water, blood, bone marrow or other materials). The supply conduit 170 may further include an optional in-line filter 174 designed to remove undesired solid materials from the fluid being treated. The filter 174 may be of any type known in the art having a structure which may be selectively varied, depending on the ultimate use for which the fluid transfer assembly 100 is intended.

Finally, the fifth port 134 as shown in FIG. 2 includes a bore 180 therein. Positioned over the bore 180 and secured to the fifth port 134 by frictional engagement therewith is a resilient, elastomeric cap member 190 having a top portion 192 axially aligned with the bore 180. The cap member 190 (e.g. manufactured from rubber or the like) is designed to function as a self-sealing septum wherein a syringe needle or comparable device (not shown) is inserted through the top portion 192 for the withdrawal or addition of fluids as desired.

With continued reference to the multi-port connector 116 of FIG. 2, the connector 116 further includes a hollow interior region 194 therein which is in fluid communication with each of the bores 122, 140, 152, 162, 180 which are all visible in FIG. 2 due to the transparent nature of the connector 116. More specifically, the hollow interior region 194 enables all of the bores 122, 140, 152, 162, 180 to communicate with each other.

The fluid transfer assembly 100 of FIG. 2 further includes a secondary vessel 200 which, in a preferred embodiment, consists of a flexible bag structure constructed of the same material and configured in the same manner as the primary vessel 102. The secondary vessel 200 further includes an interior region 202 therein designed to retain fluid inside the secondary vessel 200. Access to the interior region 202 is accomplished through the use of an outwardly extending connecting portion 204 configured in the same manner as the connecting portion 106 associated with the primary vessel 102. The connecting portion 204 has a bore 208 therein which is in fluid communication with the interior region 202 of the secondary vessel 200. Fixedly secured within the bore 208 is the proximal end 212 of a tubular connecting conduit 214.

With continued reference to FIG. 2, a second multi-port connector 216 is provided which again is preferably manufactured of an inert, biologically compatible plastic (e.g. polyvinyl chloride) that is transparent as illustrated in order to enable the observation of fluid flow therethrough. The multi-port connector 216 includes a tubular first outwardly extending port 220 having a bore 222 therein. Fixedly secured within the bore 222 is the distal end 224 of the connecting conduit 214.

The multi-port connector 216 further includes a tubular second port 226, a tubular third port 230, and a tubular fourth port 232 all of which extend outwardly from the connector 216. With continued reference to FIG. 2, the second port 226 has a bore 240 therein. Fixedly secured within the bore 240 is the proximal end 242 of a tubular third conduit 244. The third conduit 244 further includes a distal end 246 and a medial portion 250 between the proximal end 242 and the distal end 246. In a preferred embodiment, the third conduit 244 is about equal in length with the second conduit 156 and longer than the first conduit 144, with the third conduit 244 being optimally about 1.5 to 2.0 times as long as the first conduit 144.

The third port 230 further includes a bore 252 therein. Fixedly secured within the bore 252 is the proximal end 254 of a tubular fourth conduit 256. The fourth conduit 256 also includes a distal end 258 and a medial portion 260 between the proximal end 254 and the distal end 258. In a preferred embodiment, the fourth conduit 256 is about equal in length with the first conduit 144. Likewise, both the second conduit 156 and the third conduit 244 are preferably longer than the fourth conduit 256, with the second and third conduits 156, 244 being optimally about 1.5 to 2.0 times as long as the fourth conduit 256.

Finally, the fourth port 232 as shown in FIG. 2 includes a bore 262 therein. Positioned over the bore 262 and secured to the fourth port 232 by frictional engagement therewith is a resilient, elastomeric cap member 264 having a top portion 266 axially aligned with the bore 262. The cap member 264 (e.g. manufactured from rubber or the like) is comparable in structure and function to the cap member 190, and is designed to function as a self-sealing septum wherein a syringe needle or comparable device (not shown) is inserted through the top portion 266 for the withdrawal or addition of fluids as desired.

With continued reference to the second multi-port connector 216 of FIG. 2, the connector 216 further includes a hollow interior region 270 therein which is in fluid communication with each of the bores 222, 240, 252, 262 which are all visible in FIG. 2 due to the transparent nature of connector 216. More specifically, the hollow interior region 270 enables all of the bores 222, 240, 252, 262 to communicate with each other.

As illustrated in FIG. 2, the fluid transfer assembly 100 further includes a first Y-shaped tri-port connecting member 272 which is preferably transparent and preferably made of the same material used to construct the multi-port connectors 116, 216. The connecting member 272 includes an outwardly extending tubular first port 274, tubular second port 276, and tubular third port 278. With reference to FIG. 2, the first port 274 and the second port 276 are directly adjacent each other. The first port 274 includes a bore 280 therein as shown in FIG. 2. The distal end 146 of the first conduit 144 is fixedly secured within the bore 280. Likewise, the second port 276 includes a bore 282 in which the distal end 258 of the fourth conduit 256 is fixedly secured. With respect to the third port 278, a bore 284 is provided therein. Fixedly secured within the bore 284 is the proximal end 286 of a connecting tube 290 which also includes a distal end 292.

With continued reference to the tri-port connecting member 272 of FIG. 2, the connecting member 272 further includes a hollow interior region 294 therein which is in fluid communication with each of the bores 280, 282, 284 which are all visible in FIG. 2 due to the transparent nature of the connecting member 272. More specifically, the hollow interior region 294 enables all of the bores 280, 282, 284 to communicate with each other.

As further illustrated in FIG. 2, the fluid transfer assembly 100 includes a second Y-shaped tri-port connecting member 300 which is preferably transparent and made of the same material used to construct the first tri-port connecting member 272. The connecting member 300 has an outwardly extending tubular first port 302, tubular second port 304, and tubular third port 306. With reference to FIG. 2, the first port 302 and the second port 304 are directly adjacent each other. The first port 302 includes a bore 308 therein. The distal end 158 of the second conduit 156 is fixedly secured within the bore 308. Likewise, the second port 304 includes a bore 310 in which the distal end 246 of the third conduit 244 is fixedly secured. With respect to the third port 306, a bore 312 is provided therein. Fixedly secured within the bore 312 is the proximal end 314 of a connecting tube 320 which also includes a distal end 322.

With continued reference to the tri-port connecting member 300 of FIG. 2, the connecting member 300 further includes a hollow interior region 324 therein which is in fluid communication with each of the bores 308, 310, 312 which are all visible in FIG. 2 due to the transparent nature of the connecting member 300. More specifically, the passageway 324 enables all of the bores 308, 310, 312 to communicate with each other.

As shown in FIG. 2, distal end 292 of the connecting tube 290 is operatively connected to and fluid communication with the outlet port 329 of a selected fluid treatment unit 330 (schematically illustrated in FIG. 2). The fluid treatment unit 330 may consist of a wide variety of different commercially available systems ranging from apheresis systems for selectively removing various components from bodily fluids (e.g. the removal of mononuclear cells from bone marrow) to water/liquid waste treatment units (e.g. wherein flocculation or filtration of suspended solids takes place). While the use of specific fluid treatment units will be described herein below, it should be noted that the present invention shall not be limited to the use of any particular or specific fluid treatment unit. Accordingly, the invention as described herein is prospectively applicable to a wide variety of conventional units/systems in which the multiple passage of a fluid therein for treatment purposes is desired or necessary.

With continued reference to FIG. 2, the fluid treatment unit 330 will preferably include at least one pump 332 (e.g. of the conventional peristaltic variety), separator means 336 (e.g. a conventional centrifuge, filtration membrane, settling chamber and the like), and a delivery line or conduit 338 through which collected materials may be routed to a storage vessel (not shown) or other desired location. In addition, the fluid treatment unit 330 further includes an inlet port 340 which is operatively connected to and in fluid communication with the distal end 322 of the connecting tube 320.

In order to facilitate the operation and use of the fluid transfer assembly 100 as described herein, it is desired that all of the main tubular conduits used in the assembly 100 (e.g. the first conduit 144, second conduit 156, third conduit 244, and fourth conduit 256) be organized in an integral, compact arrangement in order to form the unitary, loop-like conduit configuration 342 illustrated in FIG. 2. As shown, the conduit configuration 342 does not include any outwardly extending or dangling conduits which tend to interfere with the effective use, storage, and operation of the fluid transfer assembly 100. In order to produce the specific configuration 342 illustrated in FIG. 2, various conduits are preferably attached to each other in a selected arrangement to produce a preferred embodiment of the present invention. With continued reference to FIG. 2, at least one first attachment means 343 is provided for securing the medial portion 160 of the second conduit 156 to the medial portion 250 of the third conduit 244 so that they are positioned directly adjacent to and against each other as shown. The second conduit 156 is oriented with respect to the third conduit 244 so that the respective proximal ends 154, 242 of the second and third conduits 156, 244 are towards opposite sides of the first attachment means 343. In a preferred embodiment, the first attachment means 343 is secured to the medial portion 160 of the second conduit 156 at a first position 346 thereon, while the first attachment means 343 is secured to the medial portion 250 of the third conduit 244 at a first position 348 thereon. Furthermore, the first attachment means 343 may encompass a wide variety of different attachment structures known in the are including a portion 350 of conventional plastic adhesive tape (e.g. commercially available from Safety Supply American of Denver Colo. (USA) and sold under the name "MICRANOVA" which is wrapped entirely around the second conduit 156 and the third conduit 244 one or more times. Likewise, the first attachment means 343 may involve the use of other structures, including but not limited to metal or plastic clips, rubber/plastic bands, wire members, string, and the like which are secured around the conduits 156, 244. Also, while the embodiment shown in FIG. 2 involves the use of a single first attachment means 343 (e.g. a single portion 350 of tape), multiple structures may be used to secure the conduits 156, 244 together.

In addition, at least one second attachment means 352 is provided for securing the medial portion 150 of the first conduit 144 to the medial portion 250 of the third conduit 244 as illustrated. In a preferred embodiment, the second attachment means 352 is secured to the medial portion 150 of the first conduit 144 at position 354 thereon. Likewise, the second attachment means 352 is secured to the medial portion 250 of the third conduit 244 at a second position 360 thereon which is remotely spaced from the first position 348 and between the first position 348 and the tri-port connecting member 300. The first and third conduits 144, 244 are oriented with respect to each other at the second attachment means 352 so that the distal ends 146, 246 of the first and third conduits 144, 244 are towards the same side of the second attachment means 352.

Furthermore, the second attachment means 352 may encompass a wide variety of different attachment structures known in the art including a portion 362 of conventional plastic adhesive tape (e.g. of the same type as portion 350 of tape) which is wrapped entirely around the first conduit 144 and the third conduit 244 one or more times. The second attachment means 352 may also involve the use of other structures, including but not limited to metal or plastic clips, rubber/plastic bands, wire members, string, and the like which are secured around the conduits 144, 244. Also, while the embodiment shown in FIG. 2 involves the use of a single second attachment means 352 (e.g. a single portion 362 of tape), multiple structures may be used to secure the conduits 144, 244 together.

Finally, at least one third attachment means 364 is provided for securing the medial portion 260 of the fourth conduit 256 to the medial portion 160 of the second conduit 156 as illustrated. In a preferred embodiment, the third attachment means 364 is secured to the medial portion 260 of the fourth conduit 256 at position 366 thereon. Likewise, the third attachment means 364 is secured to the medial portion 160 of the second conduit 156 at a second position 368 thereon which is remotely spaced from the first position 346 and between the first position 346 and the tri-port connecting member 300. The second and fourth conduits 156, 256 are oriented with respect to each other so that the distal ends 158, 258 of the second and fourth conduits 156, 256 are towards the same side of the third attachment means 364.

The third attachment means 364 may likewise encompass a wide variety of different attachment structures known in the art including a portion 370 of conventional plastic adhesive tape (e.g. of the same type as portion 350 of tape) which is wrapped entirely around the second conduit 156 and the fourth conduit 256 one or more times. The third attachment means 364 may also involve the use of other structures, including but not limited to metal or plastic clips, rubber/plastic bands, wire members, string, and the like which are secured around the conduits 156, 256. Also, while the embodiment shown in FIG. 2 involves the use of a single third attachment means 364 (e.g. a single portion 370 of tape), multiple structures may be used to secure the conduits 156, 256 together.

By using the first attachment means 343, the second attachment means 352, and the third attachment means 364 in the manner described above, the loop-like conduit configuration 342 may be readily produced. Likewise, production of the conduit configuration 342 illustrated in FIG. 2 is facilitated by the fact that (1) the third conduit 244 has a length which is greater than the length of the first conduit 144; (2) the second conduit 156 has a length which is greater than the length of the fourth conduit 256; (3) the second conduit 156 and the third conduit 244 are about equal in length; and (4) the first conduit 144 and the fourth conduit 256 are about equal in length. It should also be noted that the foregoing arrangement of conduits in the configuration 342 enables selected multiple conduits (e.g. conduit pairs) to be clamped simultaneously in accordance with the present invention as will be described in greater detail below.

Finally, as illustrated in the embodiment of FIG. 2, the fluid transfer assembly 100 further includes means for providing a rapid and definitive indication as to which conduits are used to deliver fluid from the outlet port 329 and to the inlet port 340 of the fluid treatment unit 330. With continued reference to FIG. 2, the first conduit 144 includes indicia 371 thereon in the form of a stripe 372 extending continuously from the proximal end 142 to the distal end 146. The indicia 371 may also involve numerous alternative forms, including but not limited to a continuous arrangement of dashes, dots, and the like. However, regardless of the type of indicia 371 which is used, it is preferred that the indicia 371 be displayed in a first color (e.g. blue).

Likewise, the fourth conduit 256 includes indicia 374 thereon which is preferably in the same form as indicia 371. In a preferred embodiment, the indicia 374 will consist of a stripe 376 extending continuously from the proximal end 254 to the distal end 258 of the fourth conduit 256. The indicia 374 may also involve the same alternative forms set forth above with respect to indicia 371. It is likewise preferred that the indicia 374 be displayed in the first color set forth above (e.g. blue) so that the indicia 371 and indicia 374 are both of the same color. This unitary color scheme enables an operator of the fluid transfer assembly 100 to rapidly and accurately determine which conduits lead into the outlet port 329 of the fluid treatment unit 330.

In a similar manner, the second conduit 156 has indicia 378 thereon which is preferably in the form of a stripe 380 which extends continuously from the proximal end 154 to the distal end 158. The indicia 378 may also be configured in the same alterative forms set forth above relative to indicia 371 and indicia 374. In addition, it is preferred that the indicia 378 be displayed in a second color (e.g. red) which is different from the first color set forth above.

Finally, the third conduit 244 has indicia 384 thereon which is preferably in the form of a stripe 386 which extends continuously from the proximal end 242 to the distal end 246. Once again, the indicia 384 may be configured in the same alternative forms described above relative to indicia 371, indicia 374, and indicia 378, although it is preferred that indicia 378 and indicia 384 be presented in identical form. It is likewise preferred that the indicia 384 be displayed in the second color set forth above (e.g. red) so that the indicia 378 and indicia 384 are both of the same color. This unitary color scheme enables an operator of the fluid transfer assembly 100 to rapidly and accurately determine which conduits are operatively connected to the inlet port 340 of the fluid treatment unit 330.

Figure 3:
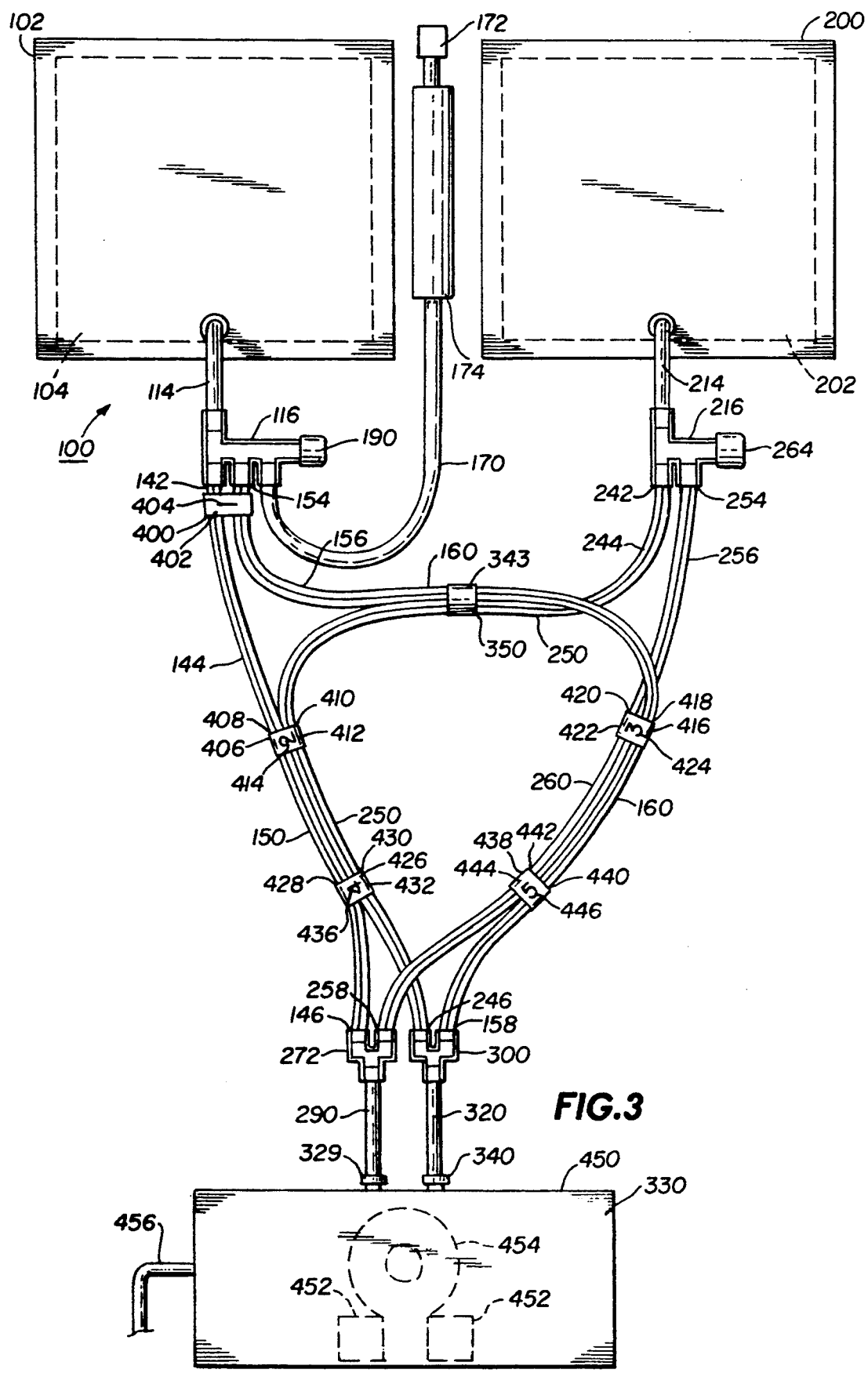
FIG. 3 illustrates a further preferred embodiment of a fluid transfer assembly produced in accordance with the invention which enables the multiple passage of a fluid through a selected fluid treatment unit.

FIG. 3 illustrates another preferred embodiment of the fluid transfer assembly 100. All of the components and functional features of the embodiment of FIG. 3 are identical to the embodiment of FIG. 2 unless otherwise indicated.

With reference to FIG. 3, included are a plurality of clamp position indicating members which are designed to facilitate proper placement of the single clamp used in connection with the fluid transfer assembly 100 as described below. As shown in FIG. 3, a first clamp position indicating member 400 is attached to both the first conduit 144 and the second conduit 156 near (e.g. adjacent) the proximal ends 142, 154 thereof so that the conduits 144, 156 are positioned adjacent to and against each other. In a preferred embodiment, the first clamp position indicating member 400 will consist of a portion 402 of conventional adhesive tape (e.g. of the same type used in connection with portion 350 of tape described above) wrapped around the first conduit 144 and the second conduit 156 one or more times. In an alternative embodiment, the first clamp position indicating member 400 (and all of the other clamp position indicating members set forth herein) may consist of a wide variety of different structures including but not limited to tags, bands, or labels (made of plastic, rubber, paper, or metal), clip members made of plastic or metal, and or other comparable structures which are secured to the conduits of interest. Accordingly, the present invention shall not be exclusively limited to the use of adhesive tape materials with respect to the clamp position indicating members set forth herein. In a preferred embodiment, the first clamp position indicating member 400 will include numeric or alphabet indicia 404 thereon indicating the order of clamp placement during use of the fluid transfer assembly 100. As shown in FIG. 3, indicia 404 may consist of the number "1", although the letter "A" may alternatively be used (not shown).

Next, a second clamp position indicating member 406 is attached to both the medial portion 150 of the first conduit 144 at position 408 thereon and the medial portion 250 of the third conduit 244 at position 410 thereon so that the first and third conduits 144, 244 are adjacent to and against each other. In a preferred embodiment the second clamp position indicating member 406 will again consist of a portion 412 of conventional adhesive tape (e.g. of the same type used in connection with portion 402 of tape) which is wrapped around the first conduit 144 and the third conduit 244 one or more times. The second clamp position indicating member 406 may also involve the use of other materials aside from the portion 412 of tape as listed above. Furthermore, in a preferred embodiment, the second clamp position indicating member 406 will include numeric or alphabet indicia 414 thereon indicating the order of clamp placement during use of the fluid transfer assembly 100. As shown in FIG. 3, exemplary indicia 414 will consist of the number "2", although the letter "B" may alternatively be used (not shown).

A third clamp position indicating member 416 is attached to both the medial portion 160 of the second conduit 156 at position 418 thereon and the medial portion 260 of the fourth conduit 256 at position 420 thereon so that the second and fourth conduits 156, 256 are adjacent to and against each other. In a preferred embodiment, the third clamp position indicating member 416 will again consist of a portion 422 of conventional adhesive tape (e.g. of the same type used in connection with portion 402 of tape) which is wrapped around the second conduit 156 and the fourth conduit 256 one or more times. The third clamp position indicating member 416 may also involve the use of other materials aside from the portion 422 of tape as listed above. Furthermore, in a preferred embodiment, the third clamp position indicating member 416 will again include numeric or alphabet indicia 424 thereon indicating the order of clamp placement during use of the fluid transfer assembly 100. As shown in FIG. 3, exemplary indicia 424 will consist of the number "3", although the letter "C" may alternatively be used (not shown).

Optional additional clamp position indicating members may also be used in connection with the fluid transfer assembly 100. For example, as shown in FIG. 3, a fourth clamp position indicating member 426 is attached to both the medial portion 150 of the first conduit 144 at position 428 thereon and the medial portion 250 of the third conduit 244 at position 430 thereon so that the first and third conduits 144, 244 are adjacent to and against each other. Accordingly, in the embodiment of FIG. 3, the fourth clamp position indicating member 426 is remotely spaced at a separate location from the second clamp position indicating member 406. Specifically, the fourth clamp position indicating member 426 is located between the second clamp position indicating member 406 and the tri-port connecting members 272, 300. In a preferred embodiment, the fourth clamp position indicating member 426 will again consist of a portion 432 of conventional adhesive tape (e.g. of the same type used in connection with portion 402 of tape) which is wrapped around the first conduit 144 and the third conduit 244 one or more times. The fourth clamp position indicating member 426 may also involve the use of other materials aside from the portion 432 of tape as listed above. Furthermore, in a preferred embodiment, the fourth clamp position indicating member 426 will include numeric or alphabet indicia 436 thereon indicating the order of clamp placement during use of the fluid transfer assembly 100. As shown in FIG. 3, exemplary indicia 436 will consist of the number "4", although the letter "D" may alternatively be used (not shown).

Finally, an optional fifth clamp position indicating member 438 is attached in the embodiment of FIG. 3 to both the medial portion 160 of the second conduit 156 at position 440 thereon and the medial portion 260 of the fourth conduit 256 at position 442 thereon so that the second and fourth conduits 156, 256 are adjacent to and against each other. Accordingly, in the embodiment of FIG. 3, the fifth clamp position indicating member 438 is remotely spaced at a separate location from the third clamp position indicating member 416. Specifically, the fifth clamp position indicating member 438 is located between the third clamp position indicating member 416 and the tri-port connecting members 272, 300. In a preferred embodiment, the fifth clamp position indicating member 438 will again consist of a portion 444 of conventional adhesive tape (e.g. of the same type used in connection with portion 402 of tape) which is wrapped around the second conduit 156 and the fourth conduit 256 one or more times. The fifth clamp position indicating member 438 may also involve the use of other materials aside from the portion 444 of tape as listed above. Furthermore, in a preferred embodiment, the fifth clamp position indicating member 438 will again include numeric or alphabet indicia 446 thereon indicating the order of clamp placement during use of the fluid transfer assembly 100. As shown in FIG. 3, exemplary indicia 446 will consist of the number "5", although the letter "E" may alternatively be used (not shown).

It should also be noted that, in the embodiment of FIG. 3, the second attachment means 352 (portion 362 of tape) and the third attachment means 364 (portion 370 of tape) are not present. Only the first attachment means 343 (portion 350 of tape) is present. Instead, the portions 402, 412, 422, 432, 444 of tape used as the clamp position indicating members 400, 406, 416, 426, 438 will also function as attachment means in the fluid treatment assembly 100 in view of the adhesive characteristics thereof. In this regard, the attachment means 343 (portion 350 of tape) may also be omitted if desired.

Finally, with continued reference to the embodiment of FIG. 3, the fluid treatment unit 330 will specifically involve an apheresis unit 450 in the form of a centrifugal separator unit designed to remove various components from bodily fluids (e.g. blood or bone marrow). Such a system is of particular value in the removal of mononuclear cell structures from bone marrow in order to preserve a patient's immune system during cancer treatment using radiation or chemotherapy. Numerous commercially available systems may be used for this purpose. However, an exemplary commercial system particularly well-suited for use as the apheresis unit 450 is manufactured and sold by Cobe BCT, Inc. of Lakewood Colo. (USA) under the SPECTRA trademark. The SPECTRA system is capable of performing a wide variety of separation procedures involving blood and bone marrow. The system (which is schematically illustrated at reference number 450) includes a plurality of peristaltic pumps 452 in combination with a centrifuge 454 designed to enable the selective separation of components from the bodily fluid being treated (e.g. the separation/removal of mononuclear cells from bone marrow). As schematically illustrated in FIG. 3, the apheresis unit 450 further includes a delivery line or conduit 456 through which the separated components may be withdrawn from the unit 450 for subsequent use or storage.

OPERATION

Use of the fluid transfer assembly 100 to accomplish the multiple passage of a fluid (e.g. bone marrow) through a fluid treatment unit 330 (e.g. apheresis unit 450) in accordance with the present invention will now be described. With reference to FIGS. 4a–4e, the method of the present invention will be illustrated in accordance with the fluid transfer assembly 100 of FIG. 3 wherein the multiple passage of fluid through the fluid treatment unit 330 (e.g. apheresis unit 450) will be accomplished using a single clamp.

Beginning with FIG. 4a, a clamp 458 is provided which is initially secured to the first conduit 144 and the second conduit 156 simultaneously so that the clamp 458 prevents the flow of fluid through both of the conduits 144, 156. The clamp 458 may be of any conventional type suitable for blocking fluid flow through flexible conduits as described herein, including but limited to a conventional hemostatic clamp sold by Cobe Laboratories, Inc. of Lakewood, Colo. (USA)—catalog number BCT100. In a preferred embodiment, the clamp 458 is attached simultaneously to the first conduit 144 near the proximal end 142 thereof and to the second conduit 156 near the proximal end 154 thereof as illustrated in FIG. 4. To facilitate proper clamp placement, the clamp 458 may be positioned directly on the first clamp position indicating member 400 which preferably consists of a portion 402 of tape having indicia 404 (e.g. a "1") thereon (FIG. 3). Thereafter, the interior region 104 of the primary vessel 102 is supplied with a fluid to be treated (e.g. a supply 459 [schematically illustrated] of bone marrow in this embodiment) via the supply conduit 170. If the optional filter 174 is used as described above, the fluid will pass through the filter 174 prior to entry into the primary vessel 102.

Next, as shown in FIG. 4b, the clamp 458 is removed from the first conduit 144 and the second conduit 156 when treatment of the fluid by the treatment unit 330 is desired. Specifically, the clamp 458 is secured to both the medial portion 150 of the first conduit 144 at position 408 thereon and the medial portion 250 of the third conduit 244 at position 410 thereon. In a preferred embodiment, after removal of the clamp 458 from the first conduit 144 and the second conduit 156, about 5 seconds are allowed to elapse before attachment of the clamp 458 to the first conduit 144 and the third conduit 244. This enables fluid from the primary vessel 102 to begin flowing in order to "prime" the fluid transfer assembly 100. To facilitate proper clamp placement after priming, the clamp 458 may be positioned directly on the second clamp position indicating member 406 which, as noted above, preferably consists of a portion 412 of tape having indicia 414 (e.g. a "2") thereon (FIG. 3). At this stage, the fluid will flow out of the interior region 104 of the primary vessel 102, into the second conduit 156, and into the inlet port 340 of the fluid treatment unit 330 (which, prior to this step, had been activated). Since fluid flow through the first conduit 144 is impeded by the clamp 458, fluid cannot flow into the outlet port 329 of the fluid treatment unit 330 via the first conduit 144, and can only flow into the inlet port 340 via the second conduit 156. The fluid then passes through the fluid treatment unit 330 (which, in this embodiment, consists of the apheresis unit 450), and is routed by the pumps 452 into the centrifuge 454 where desired components are removed (e.g. the removal of mononuclear cells from bone marrow). The materials removed and collected by the centrifuge 454 are then directed out of the fluid treatment unit 330 (apheresis unit 450) via the delivery conduit 456 where the collected materials are then stored or used as desired.

The remaining fluid within the fluid treatment unit 330 (after component removal therefrom) then passes through the outlet port 329, into the fourth conduit 256, and into the secondary vessel 200. Since fluid flow through the first conduit 144 (which is also connected to the outlet port 329 of the treatment unit 330) is blocked by the clamp 458, the fluid cannot pass back into the interior region 104 of the primary vessel 102 at this time.

To pass the fluid within the secondary vessel 200 back into the fluid treatment unit 330 for the enhanced removal of desired components therefrom, the clamp 458 is removed from the first conduit 144 and the third conduit 244 (e.g. removed from the second clamp position indicating member 406). Immediately thereafter (as shown in FIG. 4c), the clamp 458 is secured simultaneously to the medial portion 160 of the second conduit 156 at position 418 thereon and the medial portion 260 of the fourth conduit 256 at position 420 thereon. To facilitate proper clamp placement, the clamp 458 may be positioned directly on the third clamp position indicating member 416 which, as noted above, preferably consists of a portion 422 of tape having indicia 424 (e.g. a "3") thereon (FIG. 3). At this stage, the fluid flows out of the interior region 202 of the secondary vessel 200, into the third conduit 244, and into the inlet port 340 of the fluid treatment unit 330. Since fluid flow through the fourth conduit 256 is impeded by the clamp 458, fluid cannot flow into the outlet port 329 via the fourth conduit 256, and can only flow into the inlet port 340 via the third conduit 244. The fluid then passes through the fluid treatment unit 330 (e.g. the apheresis unit 450), and is routed by the pumps 452 into the centrifuge 454 where additional desired components (e.g. mononuclear cells from bone marrow) not removed during the first passage are removed by the apheresis unit 450. The materials removed and collected by the centrifuge 454 are then directed out of the fluid treatment unit 330 (apheresis unit 450) via the delivery conduit 456 where the collected materials are again stored or used as desired.

The remaining fluid within the fluid treatment unit 330 (after additional component removal therefrom) then passes through the outlet port 329, into the first conduit 144, and back into the interior region 104 of the primary vessel 102, thereby completing two separate passes of the fluid through the fluid treatment unit 330 in a highly efficient manner using only three movements of a single clamp 458. Since fluid flow through the fourth conduit 256 (which is also connected to the outlet port 329 of the fluid treatment unit 330) is blocked by the clamp 458, the fluid cannot pass back into the secondary vessel 200 at this time.

To complete two additional passes of the fluid through the treatment unit 330 for even further treatment/separation, the clamp 458 is removed from the second conduit 156 and the fourth conduit 256 (e.g. removed from the third clamp position indicating member 416), and is secured simultaneously to both the medial portion 150 of the first conduit 144 at position 428 thereon and the medial portion 250 of the third conduit 244 at position 430 thereon (FIG. 4d). To facilitate proper clamp placement, the clamp 458 may be positioned directly on fourth clamp position indicating member 426 which, as noted above, preferably consists of a portion 432 of tape having indicia 436 (e.g. a "4") thereon (FIG. 3). At this point, the fluid is able to flow back out of the interior region 104 of the primary vessel 102, into the second conduit 156, and into the inlet port 340 of the fluid treatment unit 330. Since fluid flow through the first conduit 144 is again impeded by the clamp 458, fluid cannot flow into the outlet port 329 via the first conduit 144, and can only flow into the inlet port 340 via the second conduit 156. The fluid then passes back through the fluid treatment unit 330 (e.g. the apheresis unit 450), and is routed by the pumps 452 into the centrifuge 454 where still further amounts of desired components (e.g. mononuclear cells) are removed which were not removed by previous passages through the apheresis unit 450. The materials removed and collected by the centrifuge 454 are then directed out of the fluid treatment unit 330 (apheresis unit 450) via the delivery conduit 456 where the collected materials are again stored or used as desired.

The remaining fluid within the fluid treatment unit 330 (after additional component removal therefrom) then passes back through the outlet port 329, into the fourth conduit 256, and into the interior region 202 of the secondary vessel 200 once again. Since fluid flow through the first conduit 144 (which is also connected to the outlet port 329 of the fluid treatment unit 330) is blocked by the clamp 458, the fluid cannot pass back into the primary vessel 102 at this time.

Finally, to pass the fluid within the secondary vessel 200 back into the fluid treatment unit 330 for still further removal of desired components therefrom, the clamp 458 is again removed from the first conduit 144 and the third conduit 244 (e.g. removed from the fourth clamp position indicating member 426), and secured simultaneously to the medial portion 160 of the second conduit 156 at position 440 thereon and the medial portion 260 of the fourth conduit 256 at position 442 thereon (FIG. 4e). To facilitate proper clamp placement, the clamp 458 may be positioned directly on the fifth clamp position indicating member 438 which, as noted above, preferably consists of a portion 444 of tape having indicia 446 (e.g. a "5" thereon). At this stage, the fluid is permitted to again flow out of the interior region 202 of the secondary vessel 200, into the third conduit 244, and into the inlet port 340 of the fluid treatment unit 330. Since fluid flow through the fourth conduit 256 is impeded by the clamp 458, fluid cannot flow into the outlet port 329 via the fourth conduit 256, and can only flow into the inlet port 340 via the third conduit 244. The fluid again passes through the fluid treatment unit 330 (e.g., the apheresis unit 450), and is routed by the pumps 452 into the centrifuge 454 where even further amounts of the desired components (e.g. mononuclear cells) not removed during previous passages are removed by the apheresis unit 450. The materials removed and collected by the centrifuge 454 are then directed out of the apheresis unit 450 via the delivery conduit 456 where they are again stored or used as desired. The remaining fluid within the fluid treatment unit 330 (after additional component removal therefrom) then passes through the outlet port 329, into the first conduit 144, and back into the interior region 104 of the primary vessel 102 once again, thereby completing four separate passes of the fluid through the fluid treatment unit 330 in a highly efficient manner using only five movements of a single clamp 458. Since fluid flow through the fourth conduit 256 (which is also connected to the outlet port 329 of the fluid treatment unit 330) is blocked by the clamp 458, the fluid cannot pass back into the interior region 202 of the secondary vessel 200 at this time. Further passages of the fluid through the fluid treatment unit 330 may be accomplished by repeating the last two movements of clamp 458 set forth above as many times as desired (e.g. moving the clamp 458 back to the fourth clamp position indicating member 426 and then to the fifth clamp position indicating member 438 in a repeating, alternating manner).

As indicated above, the present invention represents a highly efficient method and apparatus for repeatedly passing a fluid through a fluid treatment unit to enhance the treatment process. More specifically, the multiple passage of a selected fluid through a fluid treatment unit is accomplished in accordance with the present invention using a minimal number of components and process steps, thereby representing an advance in the art of fluid treatment.

Having herein described preferred embodiments of the present invention, it is anticipated that suitable modifications may be made thereto by individuals skilled in the art which fall within the scope of the invention. Accordingly, the present invention shall only be construed in accordance with the following claims:

The invention that is claimed is:

1. A method for repeatedly passing a fluid through a fluid treatment unit comprising an inlet and an outlet, said inlet allowing fluid to pass into said treatment unit and said outlet allowing fluid to pass out of said treatment unit, said method comprising:

providing a fluid transfer assembly for attachment to said treatment unit comprising:

a primary vessel comprising an interior region therein;

a first conduit comprising a proximal end operatively connected to said primary vessel and in fluid communication with said interior region thereof, said first conduit further comprising a distal end operatively connected to and in fluid communication with said outlet of said treatment unit;

a second conduit comprising a proximal end operatively connected to said primary vessel and in fluid communication with said interior region thereof, said second conduit further comprising a distal end operatively connected to and in fluid communication with said inlet of said treatment unit;

a secondary vessel comprising an interior region therein;

a third conduit comprising a proximal end operatively connected to said secondary vessel and in fluid communication with said interior region thereof, said third conduit further comprising a distal end operatively connected to and in fluid communication with said inlet of said treatment unit;

a fourth conduit comprising a proximal end operatively connected to said secondary vessel and in fluid communication with said interior region thereof, said fourth conduit further comprising a distal end operatively connected to and in fluid communication with said outlet of said treatment unit; and a clamp member for simultaneously clamping at least two of said first conduit, said second conduit, said third conduit, and said fourth conduit in order to entirely restrict fluid flow therethrough;

clamping said first conduit and said second conduit simultaneously with said clamp member;

supplying said interior region of said primary vessel with a fluid to be treated;

removing said clamp member from said first conduit and said second conduit when treatment of said fluid by said treatment unit is desired;

clamping said first conduit and said third conduit simultaneously with said clamp member in order to permit said fluid to flow out of said interior region of said primary vessel, into said second conduit, and into said inlet of said treatment unit, said fluid subsequently passing through said treatment unit and outwardly therefrom through said outlet, said fluid thereafter passing from said outlet through said fourth conduit and into said interior region of said secondary vessel;

removing said clamp member from said first conduit and said third conduit; and clamping said second conduit and said fourth conduit simultaneously with said clamp member in order to permit said fluid to flow out of said interior region of said secondary vessel, into said third conduit, and into said inlet of said treatment unit, said fluid subsequently passing through said treatment unit and outwardly therefrom through said outlet, said fluid thereafter passing from said outlet through said first conduit and back into said interior region of said primary vessel.

2. A method for repeatedly passing a fluid through a fluid treatment unit comprising an inlet and an outlet, said inlet allowing fluid to pass into said treatment unit and said outlet allowing fluid to pass out of said treatment unit, said method comprising:

providing a fluid transfer assembly for attachment to said treatment unit comprising:

a primary vessel comprising an interior region therein;

a first conduit comprising a proximal end operatively connected to primary vessel and in fluid communication with said interior region thereof, said first conduit further comprising a distal end operatively connected to and in fluid communication with said outlet of said treatment unit;

a second conduit comprising a proximal end operatively connected to said primary vessel and in fluid communication with said interior region thereof, said second conduit further comprising a distal end operatively connected to and in fluid communication with said inlet of said treatment unit;

a secondary vessel comprising an interior region therein;

a third conduit comprising a proximal end operatively connected to said secondary vessel and in fluid communication with said interior region thereof, said third conduit further comprising a distal end operatively connected to and in fluid communication with said inlet of said treatment unit;

a fourth conduit comprising a proximal end operatively connected to said secondary vessel and in fluid communication with said interior region thereof, said fourth conduit further comprising a distal end operatively connected to and in fluid communication with said outlet of said treatment unit; and a clamp member for simultaneously clamping at least two of said first conduit, said second conduit, said third conduit, and said fourth conduit in order to entirely restrict fluid flow therethrough;

clamping said first conduit and said second conduit simultaneously with said clamp member;

supplying said interior region of said primary vessel with a fluid to be treated;

removing said clamp member from said first conduit and said second conduit when treatment of said fluid by said treatment unit is desired;

clamping said first conduit and said third conduit simultaneously with said clamp member in order to permit said fluid to flow out of said interior region of said primary vessel, into said second conduit, and into said inlet of said treatment unit, said fluid subsequently passing through said treatment unit and outwardly therefrom through said outlet, said fluid thereafter passing from said outlet through said fourth conduit and into said interior region of said secondary vessel;

removing said clamp member from said first conduit and said third conduit;

clamping said second conduit and said fourth conduit simultaneously with said clamp member in order to permit said fluid to flow out of said interior region of said secondary vessel, into said third conduit, and into said inlet of said treatment unit, said fluid subsequently passing through said treatment unit and outwardly therefrom through said outlet, said fluid thereafter passing from said outlet through said first conduit and back into said interior region of said primary vessel;

removing said clamp member from said second conduit and said fourth conduit;

clamping said first conduit and said third conduit simultaneously with said clamp member in order to permit said fluid to flow out of said interior region of said primary vessel, into said second conduit, and into said inlet of said treatment unit, said fluid subsequently passing through said treatment unit and outwardly therefrom through said outlet, said fluid thereafter passing from said outlet through said fourth conduit and back into said interior region of said secondary vessel;

removing said clamp member from said first conduit and said third conduit; and clamping said second conduit and said fourth conduit simultaneously with said clamp member in order to permit said fluid to flow out of said interior region of said secondary vessel, into said third conduit, and into said inlet of said treatment unit, said fluid subsequently passing through said treatment unit and outwardly therefrom through said outlet, said fluid thereafter passing from said outlet through said first conduit and back into interior region of said primary vessel.

3. A method for repeatedly passing a supply of bone marrow through a centrifugal separator unit in order to remove mononuclear cells from said bone marrow, said separator unit comprising an inlet, an outlet, and centrifuge means for removing said mononuclear cells from said bone marrow, said inlet allowing said bone marrow to pass into said separator unit and said outlet allowing said bone marrow to pass out of said separator unit after removal of said mononuclear cells therefrom, said method comprising:

providing a bone marrow transfer assembly for attachment to said centrifugal separator unit comprising:

a primary vessel comprising an interior region therein;

a first conduit comprising a proximal end operatively connected to primary vessel and in fluid communication with said interior region thereof, said first conduit further comprising a distal end operatively connected to and in fluid communication with said outlet of said separator unit;

a second conduit comprising a proximal end operatively connected to said primary vessel and in fluid communication with said interior region thereof, said second conduit further comprising a distal end operatively connected to and in fluid communication with said inlet of said separator unit;

a secondary vessel comprising an interior region therein;

a third conduit comprising a proximal end operatively connected to said secondary vessel and in fluid communication with said interior region thereof, said third conduit further comprising a distal end operatively connected to and in fluid communication with said inlet of said separator unit;

a fourth conduit comprising a proximal end operatively connected to said secondary vessel and in fluid communication with said interior region thereon, said fourth conduit further comprising a distal end operatively connected to and in fluid communication with said outlet of said separator unit; and a clamp member for simultaneously clamping at least two of said first conduit, said second conduit, said third conduit, and said fourth conduit in order to entirely restrict fluid flow therethrough;

clamping said first conduit and said second conduit simultaneously with said clamp member;

supplying said interior region of said primary vessel with a supply of bone marrow;

removing said clamp member from said first conduit and said second conduit when removal of said mononuclear cells from said bone marrow is desired;

clamping said first conduit and said third conduit simultaneously with said clamp member in order to permit said bone marrow to flow out of said interior region of said primary vessel, into said second conduit, and into said inlet of said separator unit, said bone marrow passing through said separator unit and into said centrifuge means for removing said mononuclear cells from said bone marrow, said bone marrow thereafter passing outwardly from said separator unit through said outlet after removal of said mononuclear cells therefrom, said bone marrow then passing from said outlet through said fourth conduit and into said interior region of said secondary vessel;

removing said clamp member from said first conduit and said third conduit; and clamping said second conduit and said fourth conduit simultaneously with said clamp member in order to permit said bone marrow to flow out of said interior region of said secondary vessel, into said third conduit, and into said inlet of said separator unit, said bone marrow passing through said separator unit and into said centrifuge means for removing said mononuclear cells from said bone marrow, said bone marrow thereafter passing outwardly from said separator unit through said outlet after removal of additional amounts of said mononuclear cells therefrom, said bone marrow then passing from said outlet through said first conduit and back into said interior region of said primary vessel.

4. A method for repeatedly passing a supply of bone marrow through a centrifugal separator unit in order to remove mononuclear cells from said bone marrow, said separator unit comprising an inlet, an outlet, and centrifuge means for removing said mononuclear cells from said bone marrow, said inlet allowing said bone marrow to pass into said separator unit and said outlet allowing said bone marrow to pass out of said separator unit after removal of said mononuclear cells therefrom, said method comprising:

providing a bone marrow transfer assembly for attachment to said centrifugal separator unit comprising:

a primary vessel comprising an interior region therein;

a first conduit comprising a proximal end operatively connected to primary vessel and in fluid communication with said interior region thereof, said first conduit further comprising a distal end operatively connected to and in fluid communication said outlet of said separator unit;

a second conduit comprising a proximal end operatively connected to said primary vessel and in fluid communication with said interior region thereof, said second conduit further comprising a distal end operatively connected to and in fluid communication with said inlet of said separator unit;

a secondary vessel comprising an interior region therein;

a third conduit comprising a proximal end operatively connected to said secondary vessel and in fluid communication with said interior region thereof, said third conduit further comprising a distal end operatively connected to and in fluid communication with said inlet of said separator unit;

a fourth conduit comprising a proximal end operatively connected to said secondary vessel and in fluid communication with said interior region thereof, said fourth conduit further comprising a distal end operatively connected to and in fluid communication with said outlet of said separator unit; and a clamp member for simultaneously clamping at least two of said first conduit, said second conduit, said third conduit, and said fourth conduit in order to entirely restrict fluid flow therethrough;

clamping said first conduit and said second conduit simultaneously with said clamp member;

supplying said interior region of said primary vessel with a supply of bone marrow;

removing said clamp member from said first conduit and said second conduit when removal of said mononuclear cells from said bone marrow is desired;

clamping said first conduit and said third conduit simultaneously with said clamp member in order to permit said bone marrow to flow out of said interior region of said primary vessel, into said second conduit, and into said inlet of said separator unit, said bone marrow passing through said separator unit and into said centrifuge means for removing said mononuclear cells from said bone marrow, said bone marrow thereafter passing outwardly from said separator unit through said outlet after removal of said mononuclear cells therefrom, said bone marrow then passing from said outlet through said fourth conduit and into said interior region of said secondary vessel;

removing said clamp member from said first conduit and said third conduit;

clamping said second conduit and said fourth conduit simultaneously with said clamp member in order to permit said bone marrow to flow out of said interior region of said secondary vessel, into said third conduit, and into said inlet of said separator unit, said bone marrow passing through said separator unit and into said centrifuge means for removing said mononuclear cells from said bone marrow, said bone marrow thereafter passing outwardly from said separator unit through said outlet after removal of additional amounts of said mononuclear cells therefrom, said bone marrow then passing from said outlet through said first conduit and back into said interior region of said primary vessel;

removing said clamp member from said second conduit and said fourth conduit;

clamping said first conduit and said third conduit simultaneously with said clamp member in order to permit said bone marrow to flow out of said interior region of said primary vessel, into said second conduit, and into said inlet of said separator unit, said bone marrow passing through said separator unit and into said centrifuge means for removing said mononuclear cells from said bone marrow, said bone marrow thereafter passing outwardly from said separator unit through said outlet after removal of further amounts of said mononuclear cells therefrom, said bone marrow then passing from said outlet through said fourth conduit and back into said interior region of said secondary vessel;

removing said clamp member from said first conduit and said third conduit; and clamping said second conduit and said fourth conduit simultaneously with said clamp member in order to permit said bone marrow to flow out of said interior region of said secondary vessel, into said third conduit, and into said inlet of said separator unit, said bone marrow passing through said separator unit and into said centrifuge means for removing said mononuclear cells from said bone marrow, said bone marrow thereafter passing outwardly from said separator unit through said outlet after removal of still further amounts of said mononuclear cells therefrom, said bone marrow then passing from said outlet through said first conduit and back into said primary vessel.

5. A fluid transfer assembly designed for attachment to a fluid treatment unit comprising:

a primary vessel comprising an interior region therein;

a first conduit comprising a proximal end, a distal end, and a medial portion between said proximal end and said distal end, said proximal end being operatively connected to primary vessel and in fluid communication with said interior region thereof;

a second conduit comprising a proximal end, a distal end, and a medial portion between said proximal end and said distal end, said proximal end being operatively connected to said primary vessel and in fluid communication with said interior region thereof;

a secondary vessel comprising an interior region therein;

a third conduit comprising a proximal end, a distal end, and a medial portion between said proximal end and said distal end, said proximal end being operatively connected to said secondary vessel and in fluid communication with said interior region thereof;

a fourth conduit comprising a proximal end, a distal end, and a medial portion between said proximal end and said distal end, said proximal end being operatively connected to said secondary vessel and in fluid communication with said interior region thereof;

first attachment means for securing said second conduit to said third conduit, said first attachment means being secured to said medial portion of said second conduit at a first position thereon and to said medial portion of said third conduit at a first position thereon;

second attachment means for securing said first conduit to said third conduit, said second attachment means being secured to said medial portion of said first conduit and to said medial portion of said third conduit at a second position thereon remotely spaced from said first position on said third conduit; and third attachment means for securing said second conduit to said fourth conduit, said third attachment means being secured to said medial portion of said fourth conduit and to said medial portion of said second conduit at a second position thereon remotely spaced from said first position on said second conduit.

6. The assembly of claim 5 wherein said first attachment means comprises at least one portion of adhesive tape wrapped around said second conduit and said third conduit.

7. The assembly of claim 6 wherein said second attachment means comprises at least one portion of adhesive tape wrapped around said first conduit and said third conduit.

8. The assembly of claim 7 wherein said third attachment means comprises at least one portion of adhesive tape wrapped around said second conduit and said fourth conduit.

9. The assembly of claim 5 wherein said first conduit and said fourth conduit each have indicia thereon of a first color.

10. The assembly of claim 9 wherein said second conduit and said third conduit each have indicia thereon of a second color which is different from said first color.

11. A fluid transfer assembly designed for attachment to a fluid treatment unit comprising:

a primary vessel comprising an interior region therein;

a first conduit comprising a proximal end, a distal end, and a medial portion between said proximal end and said distal end, said proximal end being operatively connected to primary vessel and in fluid communication with said interior region thereof;

a second conduit comprising a proximal end, a distal end, and a medial portion between said proximal end and said distal end, said proximal end being operatively connected to said primary vessel and in fluid communication with said interior region thereof;

a secondary vessel comprising an interior region therein;

a third conduit comprising a proximal end, a distal end, and a medial portion between said proximal end and said distal end, said proximal end being operatively connected to said secondary vessel and in fluid communication with said interior region thereof;

a fourth conduit comprising a proximal end, a distal end, and a medial portion between said proximal end and said distal end, said proximal end being operatively connected to said secondary vessel and in fluid communication with said interior region thereof;

a first clamp position indicating member attached to said first conduit adjacent said proximal end thereof and said second conduit adjacent said proximal end thereof;

a second clamp position indicating member attached to said medial portion of said first conduit and said medial portion of said third conduit; and a third clamp position indicating member attached to said medial portion of said second conduit and said medial portion of said fourth conduit.

12. The assembly of claim 11 wherein said first clamp position indicating member comprises at least one portion of adhesive tape wrapped around said first conduit and second conduit.

13. The assembly of claim 12 wherein said second clamp position indicating member comprises at least one portion of adhesive tape wrapped around said first conduit and said third conduit.

14. The assembly of claim 13 wherein said third clamp position indicating member comprises at least one portion of adhesive tape wrapped around said second conduit and said fourth conduit.

15. The assembly of claim 11 further comprising:
a fourth clamp position indicating member attached to said medial portion of said first conduit and said medial portion of said third conduit, said fourth clamp position indicating member being remotely spaced from said second clamp position indicating member; and
a fifth clamp position indicating member attached to said medial portion of said second conduit and said medial portion of said fourth conduit, said fifth clamp position indicating member being remotely spaced from said third clamp position indicating member.

16. The assembly of claim 15 wherein said fourth clamp position indicating member comprises at least one portion of adhesive tape wrapped around said first conduit and said third conduit.

17. The assembly of claim 16 wherein said fifth clamp position indicating member comprises at least one portion of adhesive tape wrapped around said second conduit and said fourth conduit.

18. The assembly of claim 11 wherein said first conduit and said fourth conduit each have indicia thereon of a first color.

19. The assembly of claim 18 wherein said second conduit and said third conduit each have indicia thereon of a second color which is different from said first color.

20. A fluid transfer assembly designed for attachment to a fluid treatment unit, said fluid treatment unit comprising an inlet and an outlet, said inlet allowing fluid to pass into said treatment unit and said outlet allowing fluid to pass out of said treatment unit, said assembly comprising:
a primary vessel comprising an interior region therein;
a first conduit comprising a proximal end operatively connected to said primary vessel and in fluid communication with said interior region thereof, said first conduit further comprising a distal end and a medial portion between said proximal end and said distal end, said distal end being operatively connected to and in fluid communication with said outlet of said treatment unit;
a second conduit comprising a proximal end operatively connected to said primary vessel and in fluid communication with said interior region thereof, said second conduit further comprising a distal end and a medial portion between said proximal end and said distal end, said distal end being operatively connected to and in fluid communication with said inlet of treatment unit, said second conduit being longer than said first conduit;
a secondary vessel comprising an interior region therein;
a third conduit comprising a proximal end operatively connected to said secondary vessel and in fluid communication with said interior region thereof, said third conduit further comprising a distal end and a medial portion between said proximal end and said distal end, said distal end being operatively connected to and in fluid communication with said inlet of said treatment unit; [and]
a fourth conduit comprising a proximal end operatively connected to said secondary vessel and in fluid communication with said interior region thereof, said fourth conduit further comprising a distal end and a medial portion between said proximal end and said distal end, said distal end being operatively connected to and in fluid communication with said outlet of said treatment unit, said third conduit being longer than said fourth conduit;
first attachment means for securing said second conduit to said third conduit, said first attachment means being secured to said medial portion of said second conduit at a first position thereon and to said medial portion of said third conduit at a first position thereon;
second attachment means for securing said first conduit to said third conduit, said second attachment means being secured to said medial portion of said first conduit and to said medial portion of said third conduit at a second position thereon remotely spaced from said first position on said third conduit; and
third attachment means for securing said second conduit to said fourth conduit, said third attachment means being secured to said medial portion of said fourth conduit and to said medial portion of said second conduit at a second position thereon remotely spaced from said first position on said second conduit.

21. The assembly of claim 20 wherein said second conduit and said third conduit are equal in length.

22. The assembly of claim 21 wherein said first conduit and said fourth conduit are equal in length.

23. The assembly of claim 20 further comprising:
a first clamp position indicating member attached to said first conduit adjacent said proximal end thereof and said second conduit adjacent said proximal end thereof;
a second clamp position indicating member attached to said medial portion of said first conduit and said medial portion of said third conduit; and a third clamp position indicating member attached to said medial portion of said second conduit and said medial portion of said fourth conduit.

24. The assembly of claim 23 further comprising:

a fourth clamp position indicating member attached to said medial portion of said first conduit and said medial portion of said third conduit, said fourth clamp position indicating member being remotely spaced from said second clamp position indicating member; and a fifth clamp position indicating member attached to said medial portion of said second conduit and said medial portion of said fourth conduit, said fifth clamp position indicating member being remotely spaced from said third clamp position indicating member.

* * * * *